United States Patent [19]

Gronvald et al.

[11] Patent Number: 5,010,090

[45] Date of Patent: Apr. 23, 1991

[54] N-(BUTENYL SUBSTITUTED) AZAHETEROCYCLIC CARBOXYLIC ACIDS

[75] Inventors: Frederik C. Gronvald, Vedbaek; Claus Braestrup, Roskilde, both of Denmark

[73] Assignee: Novo Nordisk A/S., Bagsvaerd, Denmark

[21] Appl. No.: 254,557

[22] Filed: Oct. 7, 1988

Related U.S. Application Data

[63] Continuation-in-part of Ser. No. 33,084, Feb. 24, 1987, abandoned.

[30] Foreign Application Priority Data

Jun. 26, 1985 [DK] Denmark .......................... 2883/85
Jun. 26, 1986 [DK] Denmark ............ PCT/DK86/00076

[51] Int. Cl.$^5$ ........................................ C07D 401/14
[52] U.S. Cl. ..................................... 514/326; 546/208; 546/212; 546/214; 546/193; 514/422; 548/524; 548/527
[58] Field of Search ............... 546/212, 214, 193, 208; 514/326, 422; 548/524, 527

[56] References Cited

U.S. PATENT DOCUMENTS

| 4,383,999 | 5/1983 | Bondinell | 546/213 |
| 4,514,414 | 4/1985 | Bondinell | 514/422 |
| 4,931,450 | 6/1990 | Sonnewald | 546/214 |

FOREIGN PATENT DOCUMENTS 0231996  8/1987  European Pat. Off. ............ 514/326
87/00171  1/1987  PCT Int'l Appl. .

OTHER PUBLICATIONS

Yunger et al., Jour. Pharmac. Exptc. Therap., vol. 228 (No. 1), pp. 109–115 (1984).
Burger, "Medicinal Chemistry", 2nd Ed. Interscience, N.Y. 1960, p. 43.

*Primary Examiner*—Donald G. Daus
*Attorney, Agent, or Firm*—Morris Fidelman; Franklin D. Wolffe

[57] ABSTRACT

1-Aminobut-3-en derivatives having optionally substituted furanyl, thienyl, pyridyl and/or pyrrolyl in the 4-position and 3-carboxypiperidin-1-yl, 3-carboxytetrahydropyrid-1-yl or 3 carboxymethylpyrrolidin-1-yl in the 1-position potentiate GABA-ergic neurotransmission.

10 Claims, No Drawings

N-(BUTENYL SUBSTITUTED) AZAHETEROCYCLIC CARBOXYLIC ACIDS

This application is continuation in part of our copending patent application Ser. No. 07/033,084 filed Feb. 24, 1987, now abandoned relating to novel amino acid derivatives exhibiting GABA-uptake inhibitory properties and possessing useful pharmacological properties on the central nervous system by selectively enhancing the GABA activity.

SUMMARY OF THE INVENTION

The present invention relates to novel N-(butenylsubstituted)azaheterocyclic carboxylic acids of the general formula I

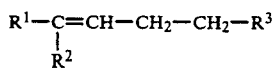

wherein $R^1$ and $R^2$ are the same or different and each represents one, two or three times by halogen or lower alkyl, and $R^3$ represents 3-carboxypiperidin-1-yl, 3-carboxy-1,2,5,6-tetrahydropyrid-1-yl or 3-carboxymethypyrrolidin-1-yl, or salts thereof.

While all of the components within the above designation exhibit the GABA uptake inhibition, it turns out that tremendous differences exist from compound to compound.

BACKGROUND OF THE INVENTION

In the last decade, intensive pharmacological research concerning γ-aminobutyric acid (hereinafter designated GABA), a neurotransmitter in the central nervous system, has taken place.

Increased GABA'ergic activity is useful in the treatment of anxiety, epilepsy and muscular and movement disorders. Furthermore, these compounds can be used as sedatives.

In U.S. Pat. Nos. 4,383,999 and 4,514,414 (Smithkline Beckman Corporation) some derivatives of N-(4-phenylbuten-3-yl)azaheterocyclic carboxylic acids which have, furthermore, inter alia, phenyl, 4-fluorophenyl, cyclohexyl or thienyl in the 4-position, are described. It is stated therein that the compounds are useful as inhibitors of GABA uptake.

According to J. Pharm. Exp. Therap., 228 (1984), 109 et seq., N-(4,4-diphenyl-3-butenyl)nipecotic acid (designated SK&F 89976A). N-(4,4-diphenyl-3-butenyl)guvacine (designated SK&F 100330A), N-(4,4-diphenyl-3-butenyl)-β-homoproline (designated SK&F 100561) and N-(4-phenyl-4-(2-thienyl)-3-butenyl)nipecotic acid (designated SK&F 100604J) are active inhibitors of GABA uptake.

It is further well recognized in the art that β-homoproline, nipecotic acid and guvacine are biological equivalents, at least as far as their GABA-like effects regards. See for example Progress in Medicinal Chemistry 21, 67-120 (1985); ed. Ellis West; Elsevier Science Publishers; Molecular and Cellular Biochemistry 31, 105-121 (1980), and J. Pharm. Exp. Therap., 228 (1984), 109 et seq. In practice of this invention they have been found to be biological equivalents.

DETAILED PRACTICE OF THIS INVENTION

It has now been found that novel compounds of the general formula exhibit GABA uptake inhibitory properties and exert useful pharmacological effects on the central nervous system, i.e., a selective enhancement of GABA activity. Compounds of formula I may be used for treatment of, for example, pain, anxiety, epilepsy, certain muscular and movement disorders, other neurological disorders and as sedatives and hypnotics.

Herein furanyl is 2-furanyl or 3-furanyl, thienyl is 2-thienyl or 3-thienyl, pyridyl is 2-pyridyl, 3-pyridyl or 4-pyridyl, and pyrrolyl is 2-pyrrolyl or 3-pyrrolyl. Furthermore, halogen is preferably, chloro, bromo and fluoro. The lower alkyl group contains less than 8 carbon atoms, preferably less than 5 carbon atoms, and especially preferred alkyl groups are methyl and ethyl. Examples of preferred substituents $R^1$ and $R^2$ are 3-methylthien-2-yl and N-methylpyrrol-2-yl.

Insofar as the inventors hereof are aware, each of the many compounds falling within the generic description will exhibit GABA uptake inhibitory properties, with, however, an extraordinary variation from compound to compound.

A great many of the compounds within the formula I have been prepared, and as has already been indicated a surprisingly large variation in GABA activity has been found to exist from compound to compound. However, the variations are not generated by differences at $R^3$. To repeat, β-homoproline, nipecotic acid and guvacine are equivalents.

Relatively small changes in $R^1$ and $R^2$ generate the variations. Thus, when $R^1$ and $R^2$ are not substituted, e.g., thien-2-yl an in vitro test value of 257 nM was found. However, when $R^2$ is changed to the 3-methylthien-2-yl the in vitro test value became 92 nM, a much superior result. Moreover, when each of $R^1$ and $R^2$ are both 3-methylthien-2-yl, an in vitro test value of 87 nM was found. Similar results were obtained when $R^1$ and/or $R^2$ were halogen substituted at the 3-position.

Surprisingly, the superior compounds all turned out to contain an ortho substitution in $R^1$ and/or $R^2$. The same substitution, at the meta position generated an inferior in vitro test value. Such occurred even when the other R contained an ortho position substituent. A sufficient number of compounds according to formula I and wherein $R^1$ and $R^2$ contain substituents have been synthesized and tested to persuade the inventors hereof that the superior to be preferred compounds are ortho substituted at $R^1$ and/or $R^2$, and, moreover, with single substitutions in $R^1$ and/or $R^2$. Such ortho substituted in $R^1$ and/or $R^2$ compounds turned out to be better than compounds unsubstituted at $R^1$, $R^2$ and far better than compounds di-substituted $R^1$, $R^2$.

Thus, the preferred compounds of this invention have been found to be compounds of formula I wherein $R^1$ and $R^2$ are the same or different and each represents furanyl, thienyl, pyridyl, pyrrolyl wherein at least one of $R^1$ and $R^2$ are ortho substituted with $C_{1-7}$-alkyl or halogen, and wherein $R^3$ represents 3-carboxypiperidin-1-yl, 3-carboxy-1,2,5,6-tetrahydropyridin-1-yl or 3-carboxymethyl-pyrrolidin-1-yl, or esters, amides or salts thereof.

Especially preferred compounds are compounds of formula I wherein $R^1$ and $R^2$ are the same or different and each represents furanyl, thienyl or pyrrolyl each of which and at least one of $R^1$ and $R^2$ are independently substituted with $C_{1-7}$-alkyl or halogen ortho to the radical position, and wherein $R^3$ represents 3-carboxypiperidin-1-yl, 3-carboxy-1,2,5,6-tetrahydropyridin-1-yl or 3-carboxymethyl-pyrrolidin-1-yl, or esters, amides or salts thereof.

Some compounds which exhibit superior properties are:

N-(4,4-Bis(3-methylthien-2-yl)but-3-enyl)guvacine,
N-(4,4-Bis(3-methylthien-2-yl)but-3-enyl)nipecotic acid,
N-(4,4-Bis(3-methylthien-2-yl)but-3-enyl)-β-homoproline,
N-(4-(3-Methylthien-2yl)-4-(thien-2-yl)but-3-enyl)guvacine,
N-(4-(3-Methylthien-2-yl)-4-(thien-2-yl)but-3-enyl)nipecotic acid,
N-(4-(3-Methylthien-2-yl)-4-(thien-2-yl)but-3-enyl)-β-homoproline,
N-(4-(N-methylpyrrol-2-yl)-4-(thien-2-yl)but-3-enyl)guvacine,
N-(4-(N-methylpyrrol-2-yl)-4-(thien-2-yl)but-3-enyl)nipecotic acid,
N-(4-(N-methylpyrrol-2-yl)-4-(thien-2-yl)but-3-enyl)-β-homoproline,
N-(4,4-Bis(N-methylpyrrol-2-yl)but-3-enyl)guvacine,
N-(4,4-Bis(N-methylpyrrol-2-yl)but-3-enyl)nipecotic acid,
N-(4,4-Bis(N-methylpyrrol-2-yl)but-3-enyl)-β-homoproline,
N-(4-(3-Bromothien-2-yl)-4-(thien-2-yl)but-3-enyl)nipecotic acid,
N-(4-(3-Bromothien-2-yl)-4-(thien-2-yl)but-3-enyl)guvacine,
N-(4-(3-Bromothien-2-yl)-4-(thien-2-yl)but-3-enyl)-β-homoproline,
N-(4,4-Bis(3-chlorothien-2-yl)but-3-enyl)guvacine,
N-(4,4-Bis(3-chlorothien-2-yl)but-3-enyl)nipecotic acid,
N-(4,4-Bis(3-chlorothien-2-yl)but-3-enyl)-β-homoproline,
N-(4,4-Bis(3-bromothien-2-yl)but-3-enyl)guvacine,
N-(4,4-Bis(3-bromothien-2-yl)but-3-enyl)nipecotic acid,
N-(4,4-Bis(3-bromothien-2-yl)but-3-enyl)-β-homoproline,
N-(4,4-Bis(3-bromothien-2-yl)but-3-enyl)guvacine,
N-(4,4-Bis(3-bromothien-2-yl)but-3-enyl)nipecotic acid,
N-(4,4-Bis(3-bromothien-2-yl)but-3-enyl)-β-homoproline,
N-(4-(3-Ethylthien-2-yl)-4-(thien-2-yl)but-3-enyl)guvacine,
N-(4-(3-Ethylthien-2-yl)-4-(thien-2-yl)but-3-enyl)nipecotic acid,
N-(4-(3-Ethylthien-2-yl)-4-(thien-2-yl)but-3-enyl)-β-homoproline,
N-(4-(3-Ethylthien-2-yl)-4-(3-methylthien-2-yl)but-3-enyl)guvacine,
N-(4-(3-Ethylthien-2-yl)-4-(3-methlthien-2-yl)but-3-enyl)nipecotic acid,
N-(4-(3-Ethylthien-2-yl)-4-(3-methylthien-2-yl)but-3-enyl)-β-homoproline,
N-(4-(N-Methylpyrrol-2-yl)-4-(3-methylthien-2-yl)but-3-enyl)guvacine,
N-(4-(N-Methylpyrrol-2-yl)-4-(3-methylthien-2-yl)but-3-enyl)nipecotic acid,
N-(4-(N-Methylpyrrol-2-yl)-4-(3-methylthien-2-yl)but-3-enyl)-β-homoproline,
n-(4,4-Bis(N-ethylpyrrol-2-yl)but-3-enyl)guvacine,
N-(4,4-Bis(N-ethylpyrrol-2-yl)but-3-enyl)nipecotic acid,
N-(4,4-Bis(N-ethylpyrrol-2-yl)but-3-enyl)-β-homoproline,
N-(4,4-Bis(N-npropylpyrrol-2-yl)but-3-enyl)guvacine,
N-(4,4-Bis(N-npropylpyrrol-2-yl)but-3-enyl)nipecotic acid,
N-(4,4-Bis(N-npropylpyrrol-2-yl)but-3-enyl)-β-homoproline,
N-(4-(3-Bromothien-2-yl)-4-(3-methylthien-2-yl)but-3-enyl)guvacine,
N-(4-(3-Bromothien-2-yl)-4-(3-methylthien-2-yl)but-3-enyl)nipecotic acid,
N-(4-(3-Bromothien-2-yl)-4-(3-methylthien-2-yl)but-3-enyl)-β-homoproline,
N-(4-(3-Chlorothien-2-yl)-4-(thien-2-yl)but-3-enyl)guvacine,
N-(4-(3-Chlorothien-2-yl)-4-(thien-2-yl)but-3-enyl)nipecotic acid,
N-(4-(3-Chlorothien-2-yl)-4-(thien-2-yl)but-3-enyl)-β-homoproline,
N-(4-(3-Chlorothien-2-yl)-4-(3-methylthien-2-yl)but-3-enyl)guvacine,
N-(4-(3-Chlorothien-2-yl)-4-(3-methylthien-2-yl)but-3-enyl)nipecotic acid,
N-(4-(3-Chlorothien-2-yl)-4-(3-methylthien-2-yl)but-3-enyl)-β-homoproline,
N-(4-(3-Chlorothien-2-yl)-4-(3-ethylthien-2-yl)but-3-enyl)guvacine
N-(4-(3-Chlorothien-2-yl)-4-(3-ethylthien-2-yl)but-3-enyl)nipecotic acid,
N-(4-(3-Chlorothien-2-yl)-4-(3-ethylthien-2-yl)but-3-enyl)-β-homoproline,
N-(4-(3-Bromothien-2-yl)-4-(3-ethylthien-2-yl)but-3-enyl)guvacine,
N-(4-(3-Bromothien-2-yl)-4-(3-ethylthien-2-yl)but-3-enyl)nipecotic acid,
N-(4-(3-Bromothien-2-yl)-4-(3-ethylthien-2-yl)but-3-enyl)-β-homoproline,
N-(4-(N-Ethylpyrrol-2-yl)-4-(3-ethylthien-2-yl)but-3-enyl)guvacine,
N-(4-(N-Ethylpyrrol-2-yl)-4-(3-ethylthien-2-yl)but-3-enyl)nipecotic acid,
N-(4-(N-Ethylpyrrol-2-yl)-4-(3-ethylthien-2-yl)but-3-enyl)-β-homoproline,
N-(4-(3-Chlorothien-2-yl)-4-(N-methylpyrrol-2-yl)but-3-enyl)guvacine,
N-(4-(3-Chlorothien-2-yl)-4-(N-methylpyrrol-2-yl)but-3-enyl)nipecotic acid,
N-(4-(3-Chlorothien-2-yl)-4-(N-methylpyrrol-2-yl)but-3-enyl)-β-homoproline,
N-(4-(3-Bromothien-2-yl)-4-(N-methylpyrrol-2-yl)but-3-enyl)guvacine,
N-(4-(3-Bromothien-2-yl)-4-(N-methylpyrrol-2-yl)but-3-enyl)nipecotic acid,
N-(4-(3-Bromothien-2-yl)-4-(N-methylpyrrol-2-yl)but-3-enyl)-β-homoproline,
N-(4,4-Bis(3-fluorothien-2-yl)but-3-enyl)guvacine,
N-(4,4-Bis(3-fluorothien-2-yl)but-3-enyl)nipecotic acid,
N-(4,4-Bis(3-fluorothien-2-yl)but-3-enyl)-β-homoproline,
N-(4-(3-Fluorothien-2-yl)-4-(3-methylthien-2-yl)but-3-enyl)guvacine,
N-(4-(3-Fluorothien-2-yl)-4-(3-methylthien-2-yl)but-3-enyl)nipecotic acid,
N-(4-(3-Fluorothien-2-yl)-4-(3-methylthien-2-yl)but-3-enyl)-β-homoproline,
N-(4,4-Bis(3-methylfuran-2-yl)but-3-enyl)guvacine,
N-(4,4-Bis(3-methylfuran-2-yl)but-3-enyl)nipecotic acid,
N-(4,4-Bis(3-methylfuran-2-yl)but-3-enyl)-β-homoproline,
N-(4-(3-Methylfuran-2-yl)-4-(3-methylthien-2-yl)but-3-enyl)guvacine, N-(4-(3-Methylfuran-2-yl)-4-(3-methylthien-2-yl)but-3-enyl)nipecotic acid,
N-(4-(3-Methylfuran-2-yl)-4-(3-methylthien-2-yl)but-3-enyl)-β-homoproline,
N-(4-(3-Methylfuran-2-yl)-4-(N-methylpyrrol-2-yl)but-3-enyl)guvacine,
N-(4-(3-Methylfuran-2-yl)-4-(N-methylpyrrol-2-yl)but-3-enyl)nipecotic acid,
N-(4-(3-Methylfuran-2-yl)-4-(N-methylpyrrol-2-yl)but-3-enyl)-β-homoproline,
N-(4-(3-Chlorothien-2-yl)-4-(3-methylfuran-2-yl)but-3-enyl)guvacine,
N-(4-(3-Chlorothien-2-yl)-4-(3-methylfuran-2-yl)but-3-enyl)nipecotic acid,
N-(4-(3-Chlorothien-2-yl)-4-(3-methylfuran-2-yl)but-3-enyl)-β-homoproline,
N-(4-(3-Bromothien-2-yl)-4-(3-methylfuran-2-yl)but-3-enyl)guvacine,
N-(4-(3-Bromothien-2-yl)-4-(3-methylfuran-2-yl)but-3-enyl)nipecotic acid,
N-(4-(3-Bromothien-2-yl)-4-(3-methylfuran-2-yl)but-3-enyl)chomoproline,
N-(4-(Furan-2-yl)-4-(3-methylthien-2-yl)but-3-enyl)-guvacine,
N-(4-(Furan-2-yl)-4-(3-methylthien-2-yl)but-3-enyl)-nipecotic acid,
N-(4-(Furan-2-yl)-4-(3-methylthien-2-yl)but-3-enyl)-chomoproline,
N-(4-(Furan-2-yl)-4-(N-methylpyrrol-2-yl)but-3-enyl)-guvacine,
N-(4-(Furan-2-yl)-4-(N-methylpyrrol-2-yl)but-3-enyl)-nipecotic acid,
N-(4-(Furan-2-yl)-4-(N-methylpyrrol-2-yl)but-3-enyl)-homoproline,
N-(4,4-Bis(2-methylthien-3-yl)but-3-enyl)guvacine,
N-(4,4-Bis(2-methylthien-3-yl)but-3-enyl)nipecotic acid,
N-(4,4-Bis(2-methylthien-3-yl)but-3-enyl)-β-homoproline,
N-(4,4-Bis(4-methylthien-3-yl)but-3-enyl)guvacine,
N-(4,4-Bis(4-methylthien-3-yl)but-3-enyl)nipecotic acid,
N-(4,4-Bis(4-methylthien-3-yl)but-3-enyl)-β-homoproline,
N-(4-(2-Methylthien-3-yl)-4-(3-methylthien-2-yl)but-3-enyl)guvacine,
N-(4-(2-Methylthien-3-yl)-4-(3-methylthien-2-yl)but-3-enyl)nipecotic acid,
N-(4-(2-Methylthien-3-yl)-4-(3-methylthien-2-yl)but-3-enyl)-β-homoproline,
N-(4-(4-Methylthien-3-yl)-4-(3-methylthien-2-yl)but-3-enyl)guvacine,
N-(4-(4-Methylthien-3-yl)-4-(3-methylthien-2-yl)but-3-enyl)nipecotic acid,
N-(4-(4-Methylthien-3-yl)-4-(3-methylthien-2-yl)but-3-enyl)-β-homoproline.

Compounds of formula I may exist as geometric and optical isomers and all isomers and mixtures thereof are included herein. Isomers may be separated by means of standard methods such as chromatographic techniques or fractional crystallization.

One embodiment of this invention is non-toxic pharmaceutically acceptable salts of compounds of formula I. Salts include those derived from inorganic or organic acids such as hydrochloric, hydrobromic, sulfuric, phosphoric, acetic, lactic, maleic and phthalic acids. Furthermore, salts include salts of the carboxylic acid group, for example sodium, potassium, calcium and magnesium salts and salts with a strong base such as triethylamine.

Compounds of formula I may be prepared by N-alkylation of a compound of the general formula II $$H-R'^3 \qquad \qquad II$$

wherein $R'^3$ has the same meaning as the above $R^3$ with the proviso that the carboxy group is protected (for example as an ester group), with a compound of the general formula III $$R^1-C=CH-CH_2-CH_2X \qquad III$$
$$\quad |$$
$$\quad R^2$$

wherein $R^1$ and $R^2$ are the same or different and each represents furanyl, thienyl, pyridyl or pyrrolyl each of which may be substituted one, two or three times by halogen or lower alkyl and X represents halogen or a tosylate residue. This reaction may be carried out in an inert solvent in the presence of an alkali metal carbonate, for example potassium carbonate, for example at reflux temperature or lower temperature, for from about 8 to 24 h. The solvent may conveniently be an alcohol, acetone or N,N-dimethylformamide. Thereafter, compounds of formula I may be prepared by hydrolysis of the resulting ester, for example by refluxing a mixture of an aqueous sodium hydroxide solution and an alcohol, such as methanol or ethanol, for from about 1 to 4 h.

Compounds of formula III may be prepared by reacting the corresponding disubstituted ketones of the general formula V $$R^1-CO-R^2 \qquad \qquad V$$

wherein $R^1$ and $R^2$ each are as defined above, with a Grignard reagent, i.e. cyclopropyl magnesium bromide, followed by ring opening and dehydration of the intermediate carbinol derivative by treatment with hydrogen bromide in acetic acid.

Or compounds of formula III may be prepared by reacting a 4-halobutyric acid ester with two eq. of an aryl Grignard reagent in f.ex. tetrahydrofuran at f.ex. −70° C. to −10° C. followed by dehydration of the intermediate carbinol in dilute acid, f.ex. ethanolic aqueous hydrochloric acid at f.ex. 40°–80° C.; or compounds of formula III may be prepared by reacting a ketone of the general formula VI $$R^4-C(O)-CH(CH_2)_2 \qquad VI$$

wherein $R^4$ is $R^1$ or $R^2$ and wherein $R^1$ and $R^2$ are as defined above, with an aryl Grignard reagent ($R^4$-MgBr for example wherein $R^4$ is as defined above) in f.ex. tetrahydrofuran at f.ex. −70° to 40° C., followed by ring opening and halogenation of the intermediate carbinol with a trialkylsilylhalogenide in for example dichloromethane at f.ex. −70° to 20° C.; or compounds of formula III may be prepared by reacting alcohols of the general formula VII $$R^1C=CHCH_2CH_2OH \qquad VII$$
$$\quad |$$
$$\quad R^2$$

wherein $R^1$ and $R^2$ each are as defined above, with a tosylchloride in f.ex. pyridine at f.ex. $-10°$ to $30°$ C.

Compounds of formula VII may be prepared by reacting a compound of formula VIII

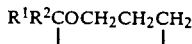

wherein $R^1$ and $R^2$ each are as defined above with dilute acid, f.ex. in aqueous ethanolic hydrochloric acid at f.ex. $40°$ to $80°$ C.

Compounds of formula VIII ($R^1=R^2$) may be prepared by reacting butyrolactone with two equivalents of an aryl Grignard reagent in f.ex. tetrahydrofuran at f.ex. reflux temperature, followed by heating with f.ex. dry hydrogen chloride in f.ex. absolute ethanol, at f.ex. $0°$ to $40°$ C.

Compounds of formula II may be prepared according to known methods, Rec. Trav. Chim. Pays. Bas. 70, 899 (1951); Acta Chem. Scand. Ser. B 35, 473 (1981) and Acta Chem. Scand. Ser. B 32, 327 (1978).

Compounds of formula I are useful because they possess pharmacological activity in man. In particular, the compounds of formula I are useful as inhibitors of GABA uptake.

For the above indications, the dosage will vary depending on the compound of formula I employed, on the mode of administration, and on the therapy desired. However, in general, satisfactory results are obtained with a dosage of from about 15 mg to about 2 g of compounds of formula I, conveniently given from 1 to 5 times daily, optionally in sustained release form. Usually, dosage forms suitable for oral administration comprise from about 25 mg to about 1 g of the compounds of formula I admixed with a pharmaceutical carrier or diluent. No toxic effects have been observed at these levels.

The compounds of formula I may be administered in pharmaceutically acceptable acid addition salt form. Such acid addition salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent. The compositions of this invention may be prepared by conventional techniques to appear in conventional forms, for example capsules or tablets.

The pharmaceutical carrier employed may be conventional or liquid carriers. Examples of solid carriers are lactose, terra alba, sucrose talc, gelatin, agar, pectin, acacia, magnesium stearate and stearic acid. Examples of liquid carriers are syrup, peanut oil, olive oil and water. Similarly, the carrier or diluent may include any time delay material well known to the art, such as glyceryl monostearate or glyceryl distearate, alone or mixed with a wax.

If a solid carrier for oral administration is used, the preparation can be tabletted, placed in a hard gelatin capsule in powder or pellet form, or in the form of a troche or lozenge. The amount of solid carrier will vary widely, but will usually be from about 25 mg to about 1 g. If a liquid carrier is used, the preparation may appear in the form of a syrup, emulsion, soft gelatin capsule or sterile injectable liquid, such as an aqueous or non-aqueous liquid suspension.

The pharmaceutical compositions of this invention can be made following the conventional techniques of the pharmaceutical industry involving mixing, granulating and compressing or variously mixing and dissolving the ingredients as appropriate to give the desired end product.

The route of administration may be any route which effectively transports the active compound to the appropriate or desired place, such as orally or parenterally, the oral route being preferred.

Any novel feature or combination of features described herein is considered essential.

The process for preparing compounds of formula I and preparations containing them is further illustrated in the following examples, which however are not to be construed as limiting. The examples illustrate some preferred embodiments.

EXAMPLE 1

(Method A)

(a) To a suspension of 1.3 g of magnesium in 20 ml of anhydrous tetrahydrofuran, 8.0 g of cyclopropyl bromide in 15 ml of anhydrous tetrahydrofuran was added under nitrogen.

The reaction mixture was kept under reflux for 1 h and then cooled to ambient temperature. To the reaction mixture 5.4 g of bis(thien-2-yl)ketone dissolved in 15 ml of anhydrous tetrahydrofuran was added dropwise. After refluxing for 30 min. the reaction mixture was chilled and 35 of a concentrated ammonium chloride solution was carefully added. To the resulting mixture 50 ml of water was added, and the suspension was extracted twice with 50 ml of ether. The ether extracts were washed with water, dried and evaporated leaving 7.6 g of an oil.

The crude product was dissolved in 60 ml of acetic acid and a mixture of 30 ml of acetic acid and 15 ml of 48% hydrobromic acid was added at 5° C. The mixture was stirred for 30 min. and then poured into 300 ml of water. The resulting emulsion was extracted twice with 100 ml of ether. The ether extracts were washed with water, dried and evaporated leaving 8.5 g of an oil.

From this oil, 5.2 g of 4,4-bis(thien-2-yl)but-3-enyl bromide having a boiling point (hereinafter b.p.) of 137° C. (0.05 mm Hg) was obtained by fractional distillation in vacuum.

(b) A suspension of 5.0 g of 4,4-bis(thien-2-yl)but-3-enyl bromide, 3.4 g of nipecotic acid ethyl ester and 3.3 g of potassium carbonate in 150 ml of dry acetone was kept under reflux for 15 h. The reaction mixture was evaporated and, after addition of 30 ml of water, the resulting solution was extracted twice with 50 ml of ethyl acetate. The ethyl acetate extracts were dried and evaporated leaving 7.3 g of an oil. By column chromatography on silica gel using methanol as eluent, N-(4,4-bis(thien-2-yl)but-3-enyl)nipecotic acid ethyl ester was isolated.

5.3 g of this compound was dissolved in 100 ml of ethanol and 200 ml of an 8N sodium hydroxide solution was added. The mixture was heated at reflux for 1 h, cooled and acidified by adding 10% hydrochloric acid. The resulting solution was evaporated and 100 ml of water was added to the residue. The resulting acid solution was extracted with ethyl acetate and the dried extract was evaporated to give N-(4,4-bis-(thien-2-yl)but-3-enyl)nipecotic acid hydrochloride.

EXAMPLE 2

(Method B)

A solution of 34 ml of n-butyllithium in 30 ml of anhydrous ether was cooled to −65° C. under nitrogen and 5.3 ml of 3-methyl- 2-bromothiophene in 10 ml anhydrous ether was added dropwise over a period of 10 min. The reaction mixture was stirred at −65° C. for 1 h and 2.7 ml of ethyl 4-bromo-butyrate in 10 ml of anhydrous ether was added slowly. The reaction was stirred for 4 h while the temperature raised to −20° C. 20 ml water was added, and the mixture was stirred for 5 min. after which the aqueous layer was removed. The ether layer was washed with 20 ml of water, and the combined aqueous phases were extracted with 50 ml of ether. The combined organic phases were dried over anhydrous sodium sulfate, which after evaporation yielded 9 g of 1-bromo-4,4-bis(3-methylthien-2-yl)but-3-ene as an oil. This compound was without further purification used for coupling with ethyl nipecotate following the procedure according to b) in Example 1, whereby N-(4,4-bis(3-methylthien-2-yl)but-3-enyl)nipecotic acid hydrochloride was obtained.

EXAMPLE 3-16

The compounds of formula I stated in table 1 below were prepared similarly to the method described in Example 1 (method A), Example 2 (method B) and Example 7 (method C).

mixture was extracted with 3×200 ml of ethyl acetate. The combined extracts were dried (MgSO$_4$) and evaporated to an oil. Flash chromatography on silica gel (Art. 9385) eluting with heptane/ethyl acetate (40:1) provided 2-(3-methylthien-2-yl)-2-(thien-2-yl)tetrahydrofuran (25.58 g, 69%) as an oil.

The above oil (25.45 g) was converted into 4-(3-methylthien-2-yl)-4-(thien-2-yl)but-3-en-1-ol by treatment with acid as described in method E. Yield (22.18 g, 87%) of an oil.

10.85 g of this oil was dissolved in 200 ml of ethanol-free chloroform and 12.52 g of p-toluenesulphonyl chloride was introduced, followed by 7.10 g of pyridine. After 24 h, 2.6 g p-toluenesulphonyl chloride was added, and after 30 h 5 ml of pyridine. After a further 24 h, 7.3 g p-toluene-sulphonyl chloride was introduced, and 17 h later the reaction was complete. The reaction mixture was evaporated and the residue purified by flash chromatography on silica gel (Art. 9385) eluting with heptane/tetrahydrofuran (19:1→10:1), to give 1-chloro-4-(3-methylthien-2-yl)-4-(thien-2-yl)but-3-ene (6.78 g, 58%) followed by the corresponding tosylate ester (1.40 g, 8%).

6.6 g of the above chlorobutene was dissolved in 200 ml of dry acetone. 5.2 g of dried, powdered potassium carbonate, 6.23 g of potassium iodide and 5.86 g of ethyl nipecotate were introduced and the mixture was heated at reflux for 220 h. The suspension was filtered and the filtrate was evaporated to a residue which was purified

TABLE 1

$$R^1-C=CH-CH_2-CH_2-R^3$$
$$|$$
$$R^2$$

| Ex. | R$^1$ | R$^2$ | R$^3$ | Method | M.p. °C. |
|---|---|---|---|---|---|
| 1 | thien-2-yl | thien-2-yl | R/S-NIP | A | 64-4* |
| 2 | 3-methylthien-2-yl | 3-methylthien-2-yl | R/S-NIP | B | 203-5* |
| 3 | 4-methylthien-2-yl | 4-methylthien-2-yl | R/S-NIP | B | 60-3** |
| 4 | 5-methylthien-2-yl | 5-methylthien-2-yl | R/S-NIP | B | 72-6** |
| 5 | 3-methylthien-2-yl | 4-methylthien-2-yl | R/S-NIP | A | 57-60** |
| 6 | 3-methylthien-2-yl | 4-methylthien-2-yl | GUV | A | 40-2** |
| 7 | thien-2-yl | 3-methylthien-2-yl | R/S-NIP | A,C | 86-8** |
| 8 | thien-2-yl | 3-methylthien-2-yl | GUV | A | 224-6* |
| 9 | N-methylpyrrol-2-yl | N-methylpyrrol-2-yl | R/S-NIP | A | 70-102** |
| 10 | 5-chloro-4-methylthien-2-yl | 5-chloro-4-methylthien-2-yl | R/S-NIP | B | 78-82** |
| 11 | thien-2-yl | 3-methylthien-2-yl | β-HOM | A,C | oil |
| 12 | 3-methylthien-2-yl | 3-methylthien-2-yl | β-HOM | A | oil |
| 13 | 3-methylthien-2-yl | 3-methylthien-2-yl | GUV | A | 207-9* |
| 14 | 3-methylthien-2-yl | 3-methylthien-2-yl | R-NIP | B | 187-9* |
| 15 | 3-methylthien-2-yl | 3-methylthien-2-yl | S-NIP | B | 188-9* |
| 16 | thien-2-yl | 3-bromothien-2-yl | R/S-NIP | A | — |

*crystallized from ethylacetate, iPrOH, acetone or water
** freezedried
NIP = nipecotic acid
GUV = guvacine
HOM = β-homoproline All compounds were isolated as the hydrochlorides.

EXAMPLE 7

(Method C)

To a suspension of 4.7 g of magnesium turnings in 75 ml of anhydrous tetrahydrofuran, 29.07 g of 2-bromo-3-methylthiophene in 125 ml of anhydrous tetrahydrofuran was slowly added under nitrogen.

The reaction mixture was kept under reflux for 1 h after the exotherm had subsided and cooled to ambient temperature. To the reaction mixture was added 27.85 g of 4-chloro-1-(2-thienyl)-butan-1-on in 75 ml of anhydrous tetrahydrofuran. The reaction mixture was heated at reflux for 0.5 h, cooled and 175 ml of saturated ammonium chloride solution was introduced, and the by flash chromatography on silica gel (Art 9385) eluting with cyclohexane/tetrahydrofuran (9:1) to provide the desired ester (4.09 g, 42%) as a gum.

This ester was converted into N-(4-(3-methylthien-2-yl)-4-(thien-2-yl)but-3-en-1-yl)nipecotic acid hydrochloride (4.2 g) using the procedure described in Method A.

EXAMPLE 17

(Method D)

(a) To a suspension of 2.6 g of magnesium turnings in 50 ml of anhydrous tetrahydrofuran, 18.8 g 2-bromo-3- methylthiophen in 60 ml of anhydrous tetrahydrofuran was added under nitrogen.

The reaction mixture was kept under reflux for 2 h and then cooled to ambient temperature. To the reaction mixture 14.5 g cyclopropyl-2-thienyl ketone dissolved in 70 ml of anhydrous tetrahydrofuran was added dropwise. After refluxing for 3 h 200 ml of ether, 100 ml of water and 100 ml of a concentrated ammonium chloride solution was carefully added. The resulting mixture was extracted twice with 100 ml ether. The ether extracts were washed with water, dried and evaporated leaving 25 g of an oil.

15 g of the crude product was dissolved in 225 ml of anhydrous methylene chloride and a solution of 7.6 ml trimethyl silyl bromide in 75 ml anhydrous methylene chloride was added at 10° C. The mixture was stirred for 45 min. and then poured into 600 ml of water. The methylene chloride phase was washed with water, dried and evaporated leaving 16.5 g of an oil, 4-(3-methylthien-2-yl)-4-(thien-2-yl)but-3-enyl bromide.

(b) As described in example 1b, 16.4 g of 4-(3-methylthien-2-yl)-4-(thien-2-yl)but-3-enyl bromide was allowed to react with 12.3 g of R-nipecotic acid ethyl ester. The reaction mixture was filtered and the filtrate evaporated leaving an oil. This oil was dissolved in 250 ml n-dibutylether and extracted with water, the water phase acidified with sulfuric acid and then extracted with ethylacetate. The water phase was neutralized with a solution of sodium hydroxide and the neutral water phase extracted with ethyl acetate. The ethyl acetate extracts were washed twice with water, dried and evaporated leaving 15 g. 7 g of this compound was purified by column chromatography on silica gel eluted with tetrahydrofuran/n-heptane (2:8) leaving 5.9 g R-N-(4-(3-methylthien-2-yl)-4-(thien-2-yl)but-3-enyl)nipecotic acid ethyl ester.

(c) 7 g of R-N-(4-(3-methylthien-2-yl)-4-(thien-2-yl)but-3-enyl)nipecotic acid ethyl ester was dissolved in 30 ml of anhydrous toluene and the temperature was raised to 60° C. 730 μl of methanol was added and then a solution of 2.3 ml trimethylsilyl chloride in 5 ml of anhydrous toluene was added. The reaction mixture was allowed to reach ambient temperature whereby a white solid precipitated, leaving 5.7 g R-N-(4-(3-methylthien-2-yl)-4-(thien-2-yl)but-3-enyl)nipecotic acid ethyl ester hydrochloride.

4.10 g of this compound was dissolved in 30 ml of ethanol and 3.1 ml of 12 N sodium hydroxide solution was added at 5° C. The mixture was stirred for 4 h and then evaporated. 10 ml of water and 150 ml of methylene chloride was added to the residue and the resulting emulsion acidified with 10.5 ml 12N hydrochloric acid, whereby a white solid precipitated. This material was recrystallized from 2-propanol leaving 4.9 g of R-N-(4-(3-methylthien-2-yl)-4-(thien-2-yl)but-3-enyl)nipecotic acid hydrochloride.

EXAMPLE 18

(Method E)

To a suspension of 1.42 g of magnesium turnings in 100 ml of anhydrous tetrahydrofuran, 10.6 g of 2-bromo-3-ethylthiophene (prepared as described in S. Gronowitz et.al., Chemica Scripta (1974), 5, 217–226) in 50 ml of anhydrous tetrahydrofuran was added under nitrogen.

The reaction mixture was kept under reflux for 1 h, and cooled to ambient temperature. To the reaction mixture was added 2.26 ml of γ-butyrolacetone in 30 ml of anhydrous tetrahydrofuran. After the exotherm had subsided, the reaction mixture was heated for 0.75 h, and 100 ml of saturated ammonium chloride solution was introduced. The organic phase was separated and the aqueous phase was extracted with 150 ml of ethylacetate. The combined organic phases were dried ($MgSO_4$) and evaporated to an oil (8.3 g).

This oil consisting of 1,1-bis(3-ethyl-2-thienyl)-1,4-dihydroxylbutan was mixed with 75 ml 2N hydrochloric acid solution, 75 ml tetrahydrofuran and 75 ml ethanol and heated at 50° C. for 18 h. The solution was evaporated and the resultant oil was purified by "flash" chromatography on silica gel (Art 9385) eluting with heptane/ethylacetate (5:1) to give 4,4-bis(3-ethylthien-2-yl)but-3-en-1-ol (5.4 g, 69%) as an oil.

5.4 g of this oil was dissolved in 50 ml of dry toluene. The solution was cooled to 0° C. and 6.6 ml of n-Buli (2.5M in hexane) was introduced, and the mixture kept at 0° C. for 1.5 h. A solution of 3.73 g of p-toluenesulphonyl chloride in toluene was added at 0° C. and the solution was left at 4° C. overnight before being evaporated. The residue was purified by "flash" chromatography on silica gel (Art 9385) eluting with a mixture of heptane and tetrahydrofuran (30:1→9:1) to give the desired tosylate (5.06 g, 61%).

The above p-toluenesulphonate ester (2.5 g) was mixed with 1.62 g of the R enantiomer of ethyl nipecotate and 1.6 g of powdered potassium carbonate in toluene (100 ml) and heated for 7 days at 100° C. The desired ester was isolated by flash chromatography on silica gel (Art 9385) eluting with heptane/tetrahydrofuran (19:1) giving the ester (1.8 g, 74%) as a gum.

This ester was converted into R-N-(4,4-bis(3-ethylthien-2-yl)but-3-en-1-yl)nipecotic acid hydrochloride (1.27 g), using the procedure described in Method A.

EXAMPLE 19

(Method F)

The tosylate ester isolated in Example 7 (1.36 g) was reacted with the S enantiomer of ethyl nipecotate (0.8 g), 0.86 g of potassium iodide and 0.8 g of dried, powdered potassium carbonate in 30 ml of dry acetone. The reaction mixture was heated at 50° C. for 36 h and at reflux for 24 h, filtered and the filtrate was evaporated. Flash chromatography of the residue on silica gel (Art 9385) eluting with cyclohexane/tetrahydrofuran (9:1) provided (0.75 g, 56%) of S-N-(4-(3-methylthien-2-yl)-4-(thien-2-yl)but-3-en-1-yl)nipecotic acid ethyl ester as a gum.

This ester (0.75 g) was converted into S-N-(4-(3-methylthien-2-yl)-4-(thien-2-yl)but-3-en-1-yl)nipecotic acid hydrochloride by the procedure described in Method A. The resultant residue was dissolved in dichloromethane and treated with activated charcoal. After filtering, the product precipitated and was collected by filtration (0.42 g).

The compounds of formula I stated in Table 2 below were prepared similarly to the method described in Example 17 (Method D), Example 18 (Method E) and Example 19 (Method F).

TABLE 2

$$R^1-C=CH-CH_2-CH_2-R^3$$
$$\phantom{R^1-C}|\phantom{=CH-CH_2-CH_2-R^3}$$
$$\phantom{R^1-C}R^2$$

| Ex. | R¹ | R² | R³ | Method | M.p. °C |
|---|---|---|---|---|---|
| 17 | thien-2-yl | 3-methylthien-2-yl | R-NIP | D | 210* |
| 18 | 3-ethylthien-2-yl | 3-ethylthien-2-yl | R-NIP | E | 55–60** |
| 19 | thien-2-yl | 3-methylthien-2-yl | S-NIP | F | 150–5* |
| 20 | 3-ethylthien-2-yl | 3-ethylthien-2-yl | GUV | E | 80–7** |
| 21 | 3-bromothien-2-yl | 3-bromothien-2-yl | R/S-NIP | E | 90–3** |
| 22 | 3-chlorothien-2-yl | 3-chlorothien-2-yl | R/S-NIP | E | 75–8** |

*crystallized from iPrOH or dichloromethane
**freezedried
GUV = guvacine
NIP = nipecotic acid All compounds were isolated as the hydrochlorides.
The esters prepared in Examples 8, 14 and 17 are presented in Table 3 below.

TABLE 3

$$R^1-C=CH-CH_2-CH_2-R'^3$$
$$\phantom{R^1-C}|$$
$$\phantom{R^1-C}R^2$$

| Ex. | R¹ | R² | R'³ | Method | M.p. °C |
|---|---|---|---|---|---|
| 23 | 3-methylthien-2-yl | 3-methylthien-2-yl | R-NIP ethylester | B | 118–20* |
| 24 | 3-methylthien-2-yl | thien-2-yl | R-NIP ethylester | D | 128–30* |
| 25 | 3-methylthien-2-yl | thien-2-yl | guvacine methylester | D | 196 dec.* |

*crystallized from toluene or iPrOH

The compounds presented in Table 1-3 were prepared as hydrochlorides.

EXAMPLE 26

| Preparation of Capsules | |
|---|---|
| Ingredients | Mg per Capsule |
| N-(4,4-bis(thien-2-yl)but-3-enyl)nipecotic acid | 125 |
| Magnesium stearate | 2 |
| Lactose | 200 |

The above ingredients are thoroughly mixed and placed into hard gelatin capsules. Such capsules are administered orally to subjects in need of treatment from 1–5 times daily to enhance GABA'ergic activity in the central nervous system.

EXAMPLE 27

| Preparation of Tablets | |
|---|---|
| Ingredients | Mg per Tablet |
| N-(4,4-bis(thien-2-yl)but-3-enyl)nipecotic acid | 200 |
| Corn starch | 46 |
| Polyvinyl pyrrolidone | 12 |
| Magnesium stearate | 1 |

The compound is thoroughly mixed with two thirds of the corn starch and granulated. The granules obtained are dried, mixed with the remaining ingredients and compressed into tablets.

The capsules or tablets thus prepared are administered orally. Similarly, other compounds of formula I can be used.

PHARMACOLOGICAL TEST

In Vitro Test

GABA-uptake inhibition was measured essentially as described by Fjalland (*Acta Pharmacol. et. Toxicol.* (1978), 42, 73–76) using 25 mM of 3H-GABA as a substrate. The results obtained appears from Table 4, the obtained values being from two separate experiments using 3–5 different concentrations of test compound.

In Vivo Test

Inhibition of DMCM induced convulsions was measured on female NMRI mice (20±2 g).

The test compounds were injected intraperitoneally 30 min. before an intraperitoneal injection of 15 mg/kg of DMCM. During 30 min. following the injection of DMCM, the animals were observed for the presence of clonic seizures and death. The $ED_{50}$ values representing 50% inhibition of DMCM induced clonic convulsions are presented in Table 5.

TABLE 4

$$R^1-C=CH-CH_2-CH_2-R^3$$
$$\phantom{R^1-C}|$$
$$\phantom{R^1-C}R^2$$

| Compound | R¹ | R² | R³ | IC₅₀ (nM) |
|---|---|---|---|---|
| 1 | 3-methylthien-2-yl | thien-2-yl | R/S-nipecotic acid | 92 |
| 2 | N-methylpyrrol-2-yl | N-methylpyrrol-2-yl | R/S-nipecotic acid | 52 |
| 3 | 3-methylthien-2-yl | thien-2-yl | guvacine | 134 |

TABLE 4-continued $$R^1-\underset{R^2}{\underset{|}{C}}=CH-CH_2-CH_2-R^3$$

| Compound | $R^1$ | $R^2$ | $R^3$ | $IC_{50}$ (nM) |
|---|---|---|---|---|
| 4 | 3-methylthien-2-yl | thien-2-yl | R/S-β-homoproline | 72 |
| 5 | 3-methylthien-2-yl | 3-methylthien-2-yl | R/S-nipecotic acid | 87 |
| 6 | 3-methylthien-2-yl | 3-methylthien-2-yl | R-nipecotic acid | 74 |
| 7 | 3-methylthien-2-yl | 3-methylthien-2-yl | R/S-β-homoproline | 69 |
| 8 | 3-bromothien-2-yl | 3-bromothien-2-yl | R/S-nipecotic acid | 96 |
| 9 | thien-2-yl | phenyl | R/S-nipecotic acid | 465 |
| | (example 18 of U.S. Pat. No. 4,383,999) | | | |
| 10 | phenyl | phenyl | R/S-nipecotic acid | 353 |
| | (example 1 of U.S. Pat. No. 4,383,999) | | | |

It is apparent from the above Table 4 that there is a close biological equivalency of nipecotic acid, guvacine and β-homoproline, among the first two by comparing compounds 1 and 3 and including β-homoproline by comparing compounds 5 and 7. It is further apparent that there is a close biological equivalency of the substituted substituents $R^1$ and $R^2$, namely thienyl and pyrrolyl. Further the compounds of the present invention as a unity are far superior over the considered closest prior art compounds (9 and 10) being in between 3 to 9 times more potent than these compounds.

TABLE 5

| Ex. | | $ED_{50}$ (mg/kg) |
|---|---|---|
| 14 | R-N-(4,4-bis(3-methylthien-2-yl)but-3-enyl)-nipecotic acid | 1.2 |
| 23 | R-N-(4,4-bis(3-methylthien-2-yl)but-3-enyl)-nipecotic acid ethyl ester | 2.5 |

It is apparent from Table 5 that ester derivatives (eg. Example 22) of compounds of formula I exert equipotency with compounds of formula I (eg. Example 14) in vivo.

We claim:
1. A compound of formula I

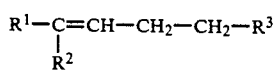    I wherein $R^1$ and $R^2$ are the same or different and each represents a substituted or unsubstituted, thien-2-yl, thien-3-yl, pyrrol-2-yl or pyrrol-3-yl wherein the substitution is with at least one of $C_{1-7}$ alkyl, bromo, chloro, or fluoro and at least one of said $R^1$ and $R^2$ is thien-2-yl substituted at least at the 3-position or pyrrol-2-yl substituted at least at the 1-position with $C_{1-7}$-alkyl, chloro, bromo, or fluoro, and wherein $R^3$ represents 3-carboxypiperidin-1-yl, 3-carboxy-1,2,5,6-tetrahydropyridin-1-yl or 3-carboxymethylpyrrolidin-1-yl, and pharmaceutically acceptable salts thereof.

2. A compound of formula I

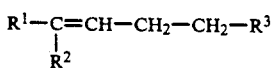    I wherein $R^1$ is 3-methylthien-2-yl, $R^2$ is 3-methylthien-2-yl and $R^1$ is nipecotic acid, and pharmaceutically acceptable salts thereof.

3. A compound of formula I

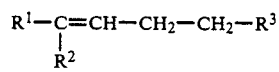    I wherein $R^1$ is thien-2-yl, $R^2$ is 3-methylthien-2-yl and $R^3$ is guvacine, and pharmaceutically acceptable salts thereof.

4. A compound of formula I

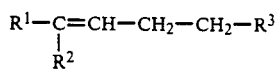    I wherein $R^1$ is thien-2-yl, $R^2$ is 3-methylthien-2-yl and $R^3$ is nipecotic acid, and pharmaceutically acceptable salts thereof.

5. A compound of formula I

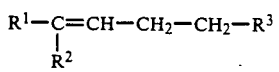    I wherein $R^1$ is 3-methylthien-2-yl, $R^2$ is 3-methylthien-2-yl and $R^3$ is guvacine, and pharmaceutically acceptable salts thereof.

6. A compound according to the following formula

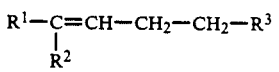    I wherein $R^1$ and $R^2$ are the same or different and each represents thienyl or pyrrolyl and wherein $R^3$ represents 3-carboxypiperidin-1-yl, 3-carboxy-1,2,5,6-tetrahydropyridin-1-yl or 3-carboxymethylpyrrolidin-1-yl, selected from the following:
N-(4,4-Bis(3-methylthien-2-yl)but-3-enyl)guvacine,
N-(4,4-Bis(3-methylthien-2-yl)but-3-enyl)nipecotic acid,
N-(4,4-Bis(3-methylthien-2-yl)but-3-enyl)-β-homoproline,
N-(4-(3-Methylthien-2-yl)-4-(thien-2-yl)but-3-enyl)guvacine,
N-(4-(3-Methylthien-2-yl)-4-(thien-2-yl)but-3-enyl)nipecotic acid,
N-(4-(3-Methylthien-2-yl)-4-(thien-2-yl)but-3-enyl)-β-homoproline
N-(4-(N-methylpyrrol-2-yl)-4-(thien-2-yl)but-3-enyl)guvacine,
N-(4-(N-methylpyrrol-2-yl)-4-(thien-2-yl)but-3-enyl)nipecotic acid, N-(4-(N-methylpyrrol-2-yl)-4-(thien-2-yl)but-3-enyl)-β-homoproline,
N-(4,4-Bis(N-methylpyrrol-2-yl)but-3-enyl)guvacine,
N-(4,4-Bis(N-methylpyrrol-2-yl)but-3-enyl)nipecotic acid,
N-(4,4-Bis(N-methylpyrrol-2-yl)but-3-enyl)-β-homoproline
N-(4-(3-Bromothien-2-yl)-4-(thien-2-yl)but-3-enyl)-nipecotic acid, and
pharmaceutically acceptable salts thereof.

7. A compound of formula I

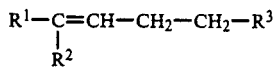

wherein $R^1$ and $R^2$ are the same or different and each represents thienyl, or pyrrolyl, and wherein $R^3$ represents 3-carboxypiperdin-1-yl, 3-carboxy-1,2,5,6-tetrahydropyridin-1-yl or 3-carboxymethyl-pyrrolidin-1-yl, selected from the following:

N-(4,4-Bis(3-Methylthien-2-yl)but-3-enyl)nipecotic acid,
N-(4,4-Bis(4-Methylthien-2-yl)but-3-enyl)nipecotic acid,
N-(4,4-Bis(5-Methylthien-2-yl)but-3-enyl)nipecotic acid,
N-(4-(3-Methylthien-2-yl)-4-(4-Methylthien-2-yl)but-3-enyl)nipecotic acid,
N-(4-(3-Methylthien-2-yl)-4-(4-Methylthien-2-yl)but-3-enyl)guvacine,
N-(4-(3-Methylthien-2-yl)-4-(thien-2-yl)but-3-enyl)nipecotic acid,
N-(4-(3-Methylthien-2-yl)-4-(4-thien-2-yl)but-3-enyl)guvacine,
N-(4,4-Bis(N-methylpyrrol-2-yl))but-3-enyl)nipecotic acid,
N-(4,4-Bis(5-chloro-4-methylpyrrol-2-yl))but-3-enyl)-nipecotic acid,
N-(4-(3-Methylthien-2-yl)-4-(thien-2-yl)but-3-enyl)-β-homoproline, and
pharmaceutically acceptable salts thereof.

8. Pharmaceutical compositions containing effective amounts of a compound according to the formula I

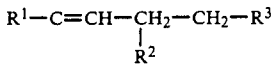

wherein $R^1$ and $R^2$ are the same or different and each represents a substituted or unsubstituted thien-2-yl, thien-3-yl, pyrrol-2-yl or pyrrol-3-yl wherein the substitution is with at least one of $C_{1-7}$ alkyl, bromo, chloro, or fluoro and at least one of said $R^1$ and $R^2$ is thien 2-yl substituted at least at the 3-position or pyrrol-2-yl substituted at least at the 1-position with $C_{1-7}$-alkyl, chloro bromo, or fluoro and wherein $R^3$ represents 3-carboxypiperidin-1-yl, 3-carboxy-1,2,5,6-tetrahydropyridin-1-yl or 3-carboxymethyl-pyrrolidin-1-yl, and pharmaceutically acceptable salts thereof.

9. Compositions according to claim 8, characterized in that they contain therein a therapeutically effective dose of from about 25 mg to about 1 g of the compound.

10. A method of inhibiting uptake of γ-amino butyric acid in a subject in need of such a treatment comprising the step of administering to said subject a therapeutically effective dose of a compound according to the formula

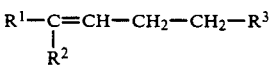

wherein $R^1$ and $R^2$ are the same or different and each represents a substituted or unsubstituted thien-2-yl, thien-3-yl, pyrrol-2-yl or pyrrol-3-yl wherein the substitution is with at least one of $C_{1-7}$ alkyl, bromo, chloro, or fluoro and at least one of said $R^1$ and $R^2$ is thien-2-yl substituted at least at the 3-position or pyrrol-2-yl substituted at least at the 1-position with $C_{1-7}$-alkyl, chloro, bromo, or fluoro and wherein $R^3$ represents 3-carboxypiperidin-1-yl, 3-carboxy-1,2,5,6-tetrahydropyridin-1-yl or 3-carboxymethylpyrrolidin-1-yl, and pharmaceutically acceptable salts thereof.

* * * * *

UNITED STATES PATENT AND TRADEMARK OFFICE
CERTIFICATE OF CORRECTION

PATENT NO. : 5,010,090
DATED : April 23, 1991
INVENTOR(S) : Novo Nordisk

It is certified that error appears in the above-identified patent and that said Letters Patent is hereby corrected as shown below:

Column 15, line 66, change "$R^1$" to --$R^3$--.

Signed and Sealed this

Twenty-third Day of November, 1999

Attest:

Q. TODD DICKINSON

*Attesting Officer*  *Acting Commissioner of Patents and Trademarks*